US008124013B1

(12) United States Patent
Gregoire et al.

(10) Patent No.: US 8,124,013 B1
(45) Date of Patent: Feb. 28, 2012

(54) SYSTEM AND METHOD FOR LARGE SCALE ATMOSPHERIC PLASMA GENERATION

(75) Inventors: Daniel J. Gregoire, Thousand Oaks, CA (US); Kevin W. Kirby, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 897 days.

(21) Appl. No.: 12/144,123

(22) Filed: Jun. 23, 2008

(51) Int. Cl.
*A61L 2/02* (2006.01)

(52) U.S. Cl. ........................ 422/21; 422/22; 204/157.15

(58) Field of Classification Search .................... 422/21, 422/22; 204/157.15
See application file for complete search history.

(56) References Cited

U.S. PATENT DOCUMENTS

| | | | | |
|---|---|---|---|---|
| 4,892,906 | A | 1/1990 | Pham et al. | |
| 5,650,461 | A | 7/1997 | Wasserman et al. | |
| 6,245,126 | B1 * | 6/2001 | Feldman et al. | 95/59 |
| 6,531,537 | B2 | 3/2003 | Friel et al. | |
| 6,917,165 | B2 * | 7/2005 | Hopwood et al. | 315/111.21 |
| 2003/0165636 | A1 * | 9/2003 | Koulik et al. | 427/569 |
| 2004/0042077 | A1 | 3/2004 | Birge et al. | |
| 2004/0164682 | A1 | 8/2004 | Hopwood et al. | |
| 2004/0175407 | A1 | 9/2004 | McDaniel | |
| 2004/0224145 | A1 | 11/2004 | Weir et al. | |
| 2004/0256056 | A1 | 12/2004 | Hall et al. | |
| 2005/0058689 | A1 | 3/2005 | McDaniel | |
| 2005/0126441 | A1 | 6/2005 | Skelhorn | |
| 2006/0141003 | A1 | 6/2006 | McDaniel | |

OTHER PUBLICATIONS

Daniels, "On the Ionization of Air for Removal of Noxious Effluvia (Air Ionization of Indoor Environments for Control of Volatile and Particulate Contaminants with Nonthermal Plasmas Generated by Dielectric-Barrier Discharge," IEEE Transactions on Plasma Science, vol. 30, No. 4, Aug. 2002, pp. 1471-1481.
Deng, et al., "Physical Mechanisms of Inactivation of *Bacillus subtilis* Spores Using Cold Atmospheric Plasmas," IEEE Transactions on Plasma Science, vol. 34, No. 4, Aug. 2006, pp. 1310-1316.
Herrmann, et al., "Chemical Warfare Agent Decontamination Studies in the Plasma Decon Chamber," IEEE Transactions on Plasma Science, vol. 30, No. 4, Aug. 2002, pp. 1460-1470.
Laroussi, "Nonthermal Decontamination of Biological Media by Atmospheric-Pressure Plasmas: Review, Analysis, and Prospects," IEEE Transactions on Plasma Science, vol. 30, No. 4, Aug. 2002, pp. 1409-1415.
Montie, et al., "An Overview of Research Using the One Atmosphere Uniform Glow Discharge Plasma (OAUGDP) for Sterilization of Surfaces and Materials," IEEE Transactions on Plasma Science, vol. 28, No. 1, Feb. 2000, pp. 41-50.

* cited by examiner

*Primary Examiner* — Sean E Conley
(74) *Attorney, Agent, or Firm* — Christie, Parker, Hale

(57) ABSTRACT

A plasma generating system and a method of generating a plasma on a surface is provided. A surface-wave medium is laminated to a surface for propagating electromagnetic surface waves. The surface-wave medium includes a dielectric and a metallic pattern on the dielectric for increasing an inductive reactance of the surface-wave medium. The plasma generating surface further includes a microwave power source. A coupler couples the microwave power source to the surface-wave medium. A plurality of field enhancement points are located on the surface-wave medium. The plurality of field enhancement points include microwave resonant structures that couple to the electromagnetic surface waves.

19 Claims, 8 Drawing Sheets

SYSTEM AND METHOD FOR LARGE SCALE ATMOSPHERIC PLASMA GENERATION

CROSS-REFERENCE TO RELATED APPLICATION(S)

This application is related to the following patent applications, all of which are incorporated herein by reference: U.S. patent application Ser. No. 12/144,052, filed Jun. 23, 2008, now U.S. Pat. No. 8,009,276, issued Aug. 30, 2011, entitled "System and Method of Surface Wave Imaging to Map Pressure on a Surface"; U.S. patent application Ser. No. 12/144,073, filed Jun. 23, 2008; now U.S. Pat. No. 7,719,694, issued May 18, 2010 entitled "System and Method of Surface Wave Imaging to Detect Ice on a Surface"; U.S. patent application Ser. No. 12/144,134, filed Jun. 23, 2008, now U.S. Pat. No. 7,931,858, issued Apr. 26, 2011, entitled "Method for Surface Decontamination Using Electromagnetic Surface Waves"; and U.S. patent application Ser. No. 12/144,170, filed Jun. 23, 2008 entitled "Method for De-icing Using Electromagnetic Surface Waves." This application is also related to U.S. patent application Ser. No. 11/324,064, filed Dec. 29, 2005, now U.S. Pat. No. 7,307,589, issued Dec. 11, 2007 entitled "Large-Scale Adaptive Surface Sensor Arrays," which is incorporated herein by reference.

BACKGROUND OF THE INVENTION

1. Field of the Invention

The present invention relates to electromagnetic surface waves, and in particular, to a system and a method for generating a plasma on a surface utilizing surface waves.

2. Description of Related Art

Common methods of generating a plasma involve using high-voltage, high-frequency power fed to electrodes in many different variations on the Tesla coil. Other methods use ultraviolet light to ionize gases such as argon. The composition of the seed gas is critical for plasma production because the plasma lifetime is dictated by its recombination rate which is affected by many factors. One such factor is the presence of gases which have an affinity for free electrons such as oxygen. While it is possible to sustain plasma indefinitely with enough continuous power, its magnitude depends on the gas composition and other external parameters such as temperature and pressure. To create a large-scale plasma covering a surface, numerous plasma generators, each powered by a separate supply must be distributed over a surface. In addition, high voltage leads are necessary to power the plasma generators. Such a plasma generator array and the attendant wiring and power are complex to utilize. Therefore, a need exists for a system and a method of large scale atmospheric plasma generation that is less complex to realize.

Further prior art related to plasmas include H. W. Hetimann, G. S. Selwyn, I. Henins, J. Park, M. Jeffery, and J. M. Williams, "Chemical Warfare Agent Decontamination Studies in the Plasma Decon Chamber," IEEE Transactions on Plasma Science, Vol. 30, No. 4, August 2002, p. 1460; T. C. Montie, K. Kelly-Wintenberg, and J. R. Roth, "An Overview of Research Using the One Atmosphere Uniform Glow Discharge Plasma (OAUGDP) for Sterilization of Surfaces and Materials," IEEE Transactions on Plasma Science, Vol. 28, No. 1, February 2000, p. 41; M. Laroussi, "Nonthermal Decontamination of Biological Media by Atmospheric-Pressure Plasmas: Review, Analysis, and Prospects," IEEE Transactions on Plasma Science, Vol. 30, No. 4, August 2002, p. 1409; X. Deng, J. Shi, M. G. Kong, "Physical Mechanisms of Inactivation of Bacillus subtilis Spores Using Cold Atmospheric Plasmas," IEEE Transactions on Plasma Science, Vol. 34, No. 4, August 2006, p. 1310; and S. L. Daniels, "On the Ionization of Air for Removal of Noxious Effluvia (Air Ionization of Indoor Environments for Control of Volatile and Particulate Contaminants with Nonthermal Plasmas Generated by Dielectric-Barrier Discharge," IEEE Transactions on Plasma Science, Vol. 30, No. 4, August 2002, p. 1471, all of which are incorporated herein by reference.

SUMMARY OF THE INVENTION

A plasma generating apparatus is provided for generating a large scale atmospheric plasma. A surface-wave medium is laminated to a surface for propagating electromagnetic surface waves. The surface-wave medium includes a dielectric and a metallic pattern on the dielectric for increasing an inductive reactance of the surface-wave medium. The plasma generating surface includes a microwave power source. A coupler couples the microwave power source to the surface-wave medium. A plurality of field enhancement points are located on the surface-wave medium.

In an exemplary embodiment of the present invention, the metallic pattern is a periodic metallic pattern of squares, rectangles, parallel or perpendicular hash marks, or Jerusalem crosses.

In an exemplary embodiment of the present invention, the metallic pattern is aperiodic.

In an exemplary embodiment of the present invention, the surface-wave medium includes a conductive ground plane between the surface and the dielectric.

In an exemplary embodiment of the present invention, the plurality of field enhancement points are powered by the electromagnetic surface waves and wherein the electromagnetic surface waves are microwave surface waves.

In an exemplary embodiment of the present invention, the plurality of field enhancement points are adapted to create a substantially surface-covering plasma layer.

In an exemplary embodiment of the present invention, the plurality of field enhancement points are comprised of microwave resonant structures that couple to the electromagnetic surface waves.

In an exemplary embodiment of the present invention, the plurality of field enhancement points are adapted to transform fields of the electromagnetic surface waves into high-field regions that ionize surrounding air or a gaseous medium.

In an exemplary embodiment of the present invention, the microwave source is a 2.45 GHz magnetron.

A method of generating a plasma on a surface is provided. A surface-wave medium is laminated to a surface for propagating electromagnetic surface waves. The surface-wave medium includes a conductive ground plane on the surface. A dielectric is provided on the conductive ground plane. A metallic pattern is provided on the dielectric for increasing an inductive reactance of the surface-wave medium. The plurality of field enhancement points are comprised of microwave resonant structures that couple to the electromagnetic surface waves. A microwave power source is provided. The electromagnetic surface waves are microwave surface waves. The microwave power source is coupled to the surface-wave medium with a coupler. A plurality of field enhancement points are located on the surface-wave medium.

In an exemplary embodiment of the present invention, a substantially surface-covering plasma layer is created that transforms fields of the electromagnetic surface waves into high-field regions that ionize surrounding air or a gaseous medium.

DETAILED DESCRIPTION

In the description below, an introduction to electromagnetic surface-wave technology, including surface-wave communication and power technology is provided. Systems and methods are then provided for generating large scale atmospheric plasma on a surface using electromagnetic surface waves.

Figure 1:
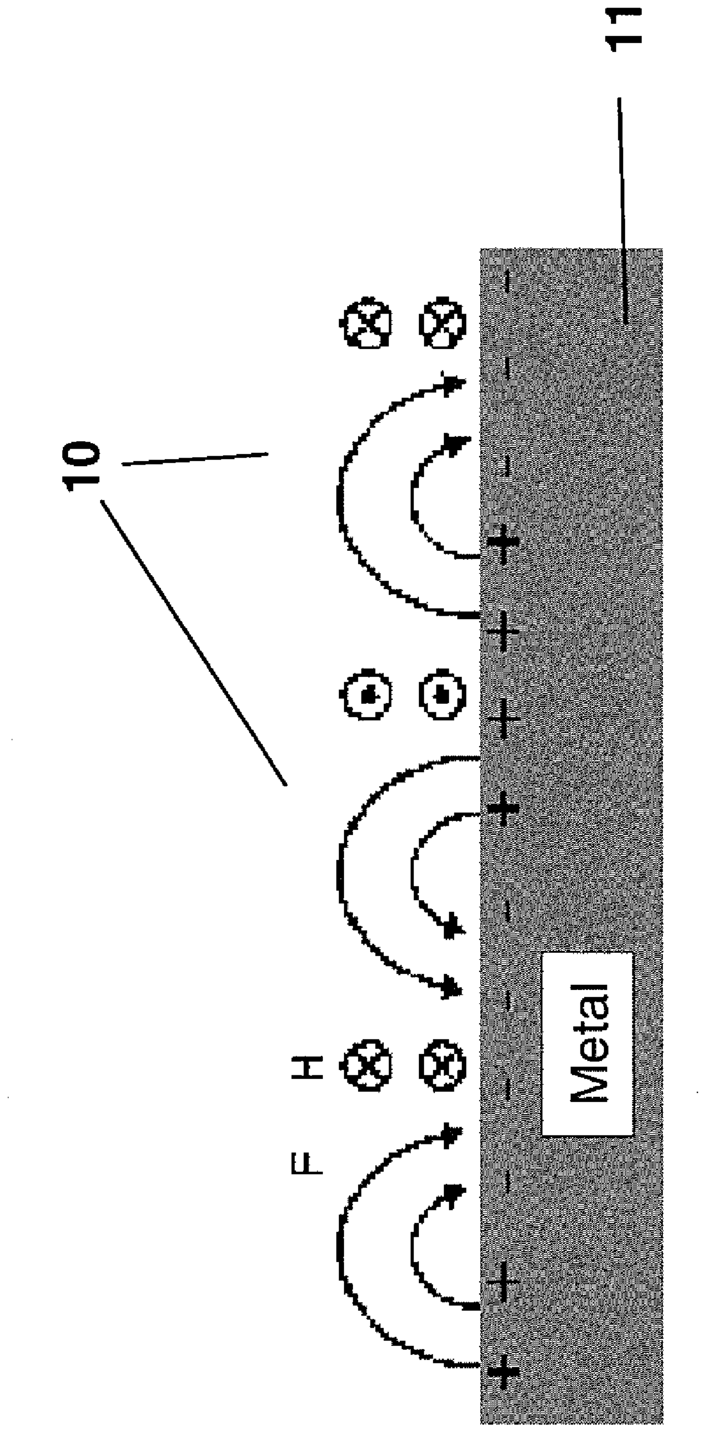
FIG. 1 depicts fields of a transverse magnetic surface wave on a flat metal surface.

FIG. 1 depicts a transverse magnetic (TM) surface wave 10 on a flat metal surface 11. A TM wave requires a surface with a surface impedance having an inductive term, while, in order to support a transverse electric (TE) surface wave, the reactive part of the surface impedance must be capacitive.

At optical frequencies, surface waves are known as surface plasmons. Surface waves are waves that are bound to the interface between a metal or other material and the surrounding space. The surface waves are characterized by longitudinally oscillating charges on the metal surface and associated fields in free space. On a flat metal surface, surface waves typically extend many thousands of wavelengths into the surrounding space. At low microwave frequencies, surface waves can extend many hundreds of meters into the surrounding space. Surfaces that allow surface waves to extend too far out into the surrounding space are not useful for wave guiding. Traditional techniques for creating surface wave media that confine fields closer to the surface generally involve thick dielectric coatings, which are not suitable for many military applications. Recent research has shown, however, that it is possible to produce thin, light-weight structures with textured-impedance surfaces that can have strong surface-wave guiding effects where the fields are confined close to the surface, do not readily leak power into free space, can follow curves in the surface, and have negligible propagation loss.

Figure 2:
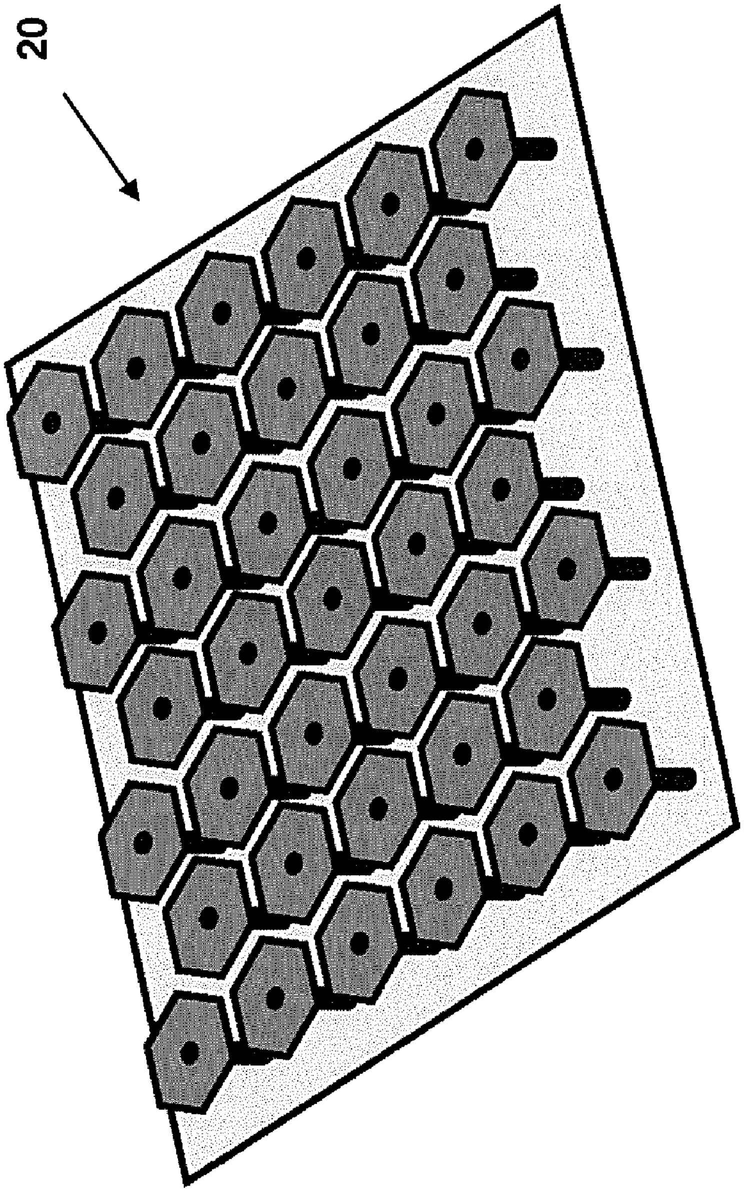
FIG. 2 depicts a periodic frequency-selective surface-wave guide having high impedance.
Figure 3:
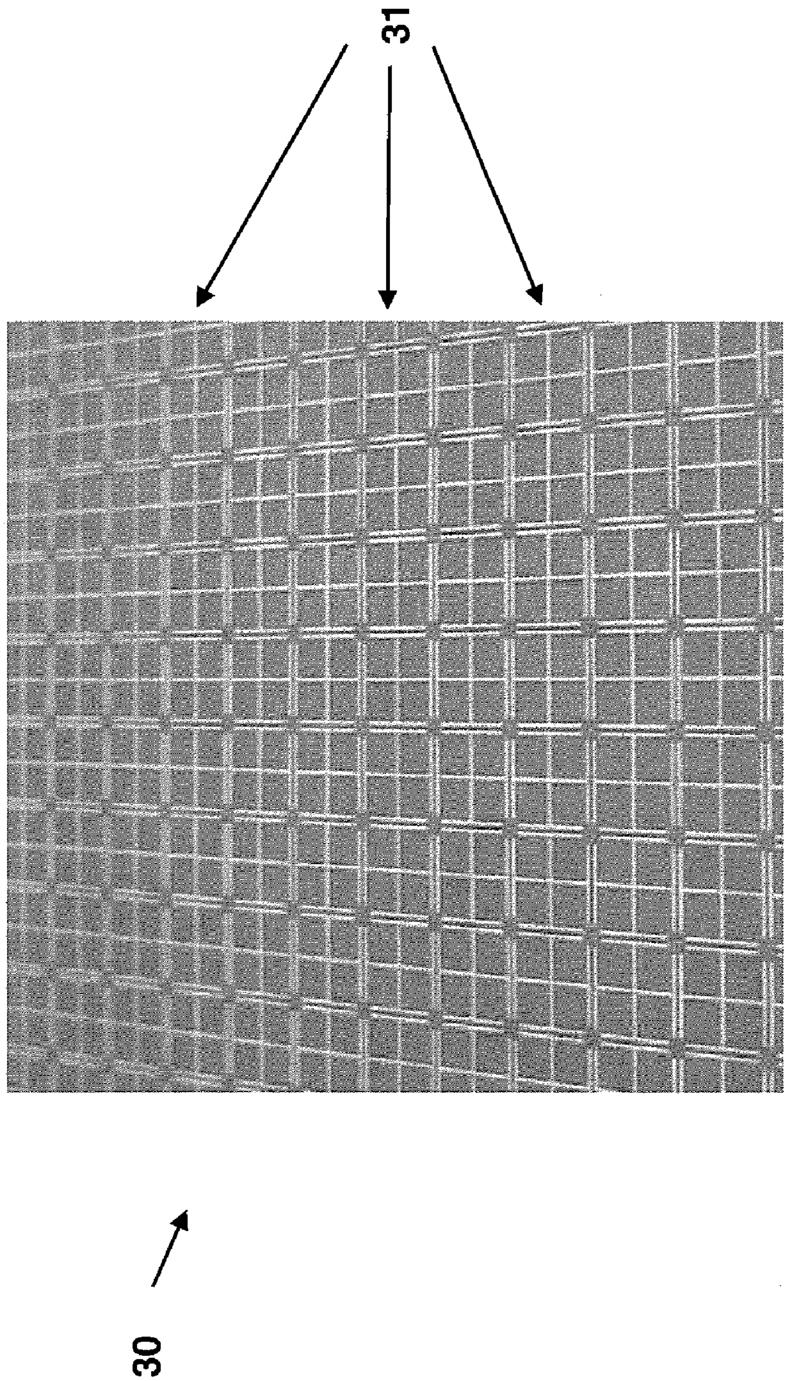
FIG. 3 depicts another periodic frequency-selective surface-wave guide having an array of Jerusalem Crosses.

FIG. 2 and FIG. 3 are two examples of textured-impedance surface geometries. A textured-impedance surface typically consists of a series of resonant structures tiled onto a thin flexible substrate. The complex geometry creates a medium that supports highly localized surface wave propagation by altering the surface impedance, such that the decay constant into free space is rapid, thus binding the wave to less than within a wavelength of the surface. A closely bound surface wave may be propagated along the surface with a small attenuation if the inductive reactance (i.e., reactive part of the surface impedance) is large and the resistance (i.e., real part of the surface impedance) is small. FIG. 2 depicts a two-layer high impedance surface-wave guide 20. FIG. 3 depicts a periodic frequency-selective surface-wave guide 30 having an array of Jerusalem Crosses 31. The surfaces depicted in FIG. 2 and FIG. 3 are inexpensive to manufacture and are readily integrated within structures.

Figure 4:
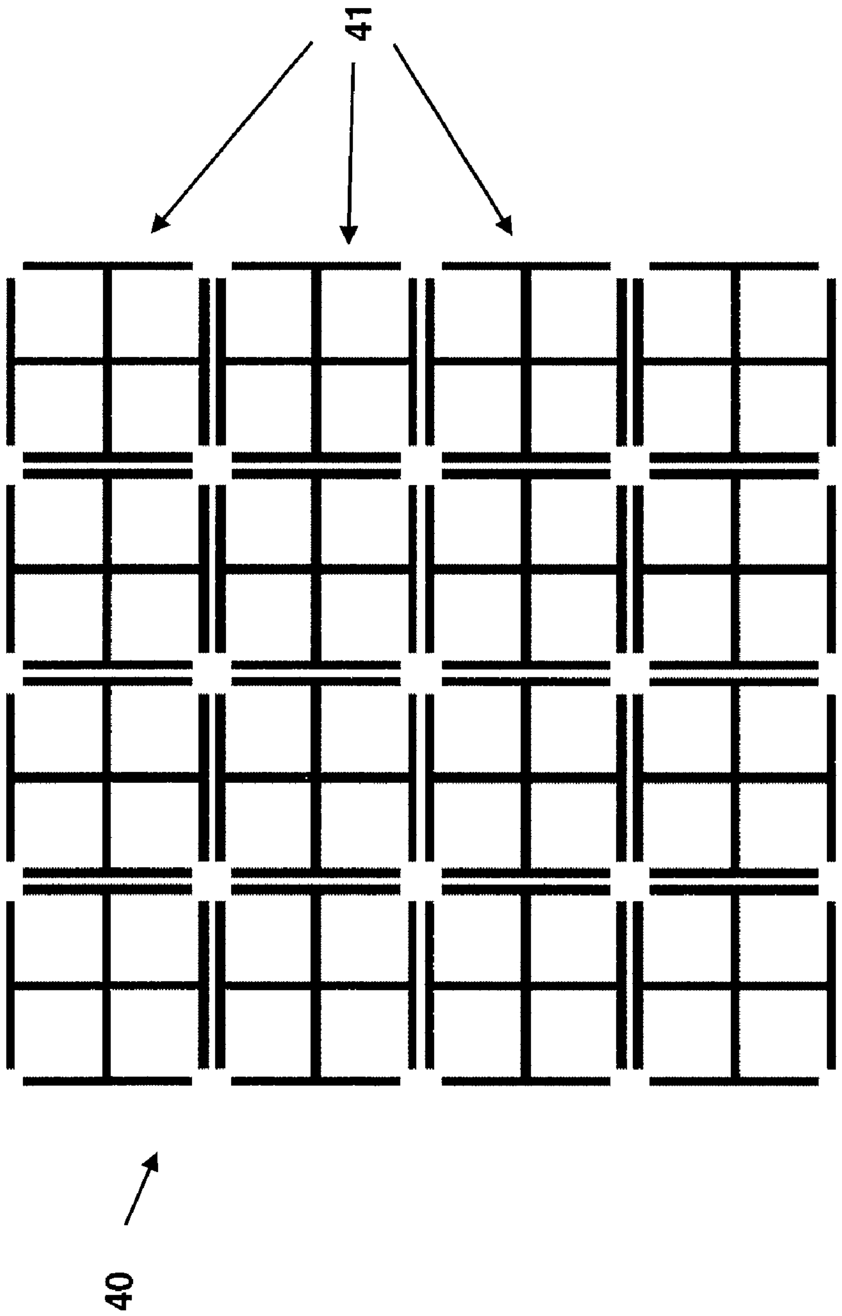
FIG. 4 is a schematic of an array of Jerusalem Crosses.
Figure 5:
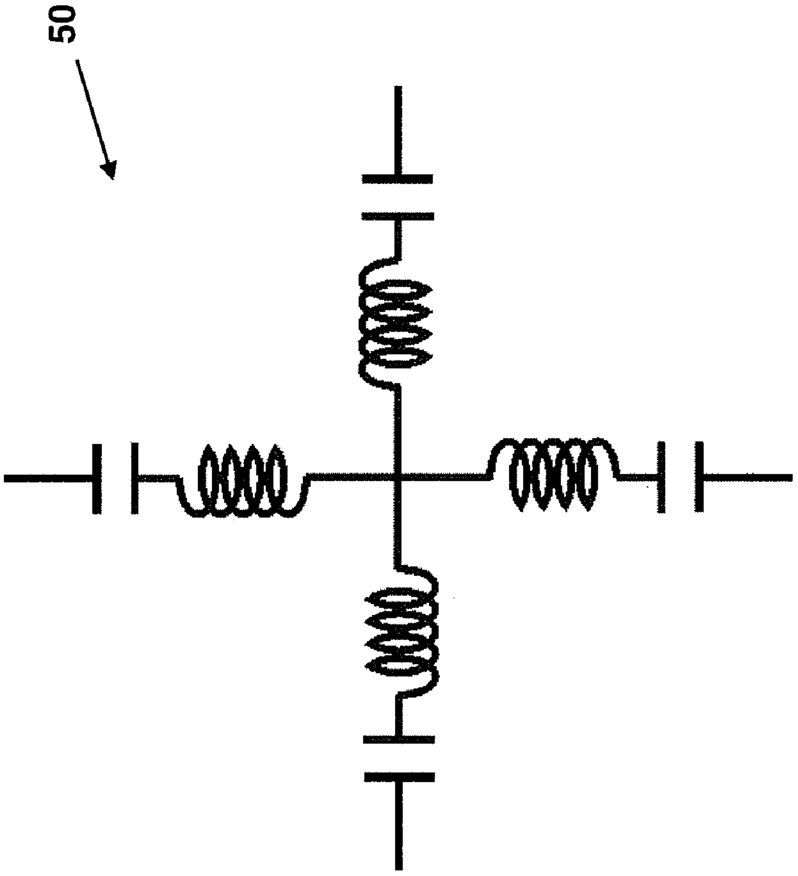
FIG. 5 is a circuit diagram depicting the equivalent circuit for the frequency selective surface-wave guide of FIG. 3.

FIG. 4 is a schematic of an array 40 of Jerusalem Crosses 41. FIG. 5 is a circuit diagram depicting the equivalent circuit for the frequency selective surface-wave guide 30 of FIG. 3.

Figure 6:
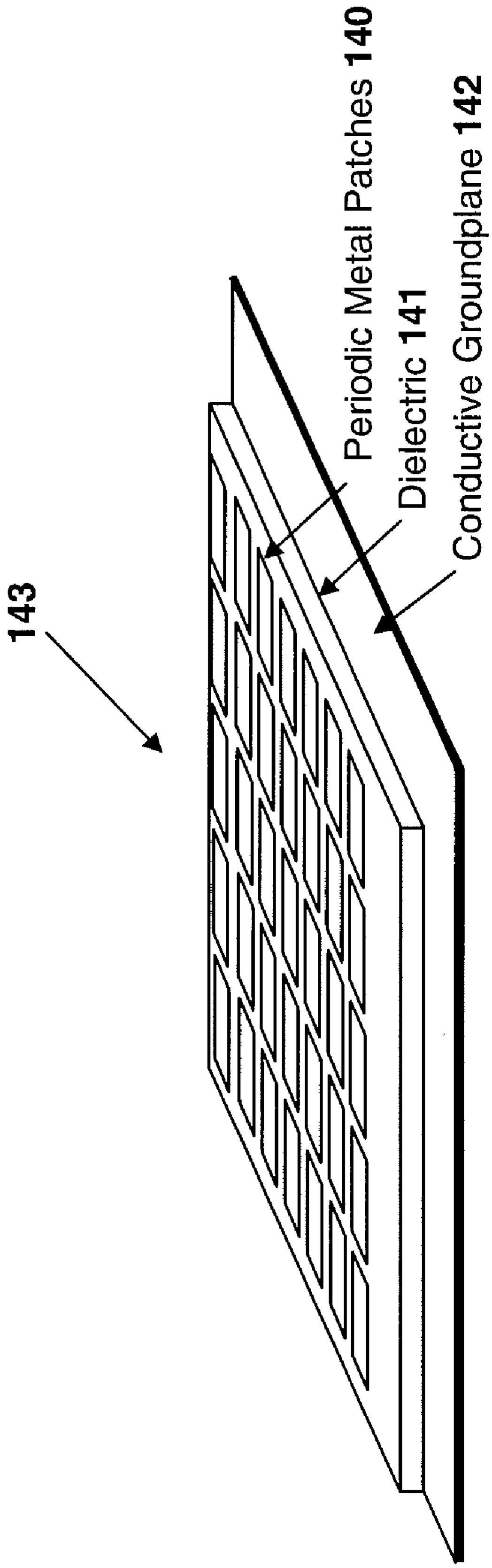
FIG. 6 depicts a surface-wave medium.

FIG. 6 depicts a surface-wave medium 143. A surface wave medium 143 is created by printing a periodic metallic pattern 140 on a dielectric material 141. The periodic metallic pattern 140 may be squares as depicted in FIG. 6, Jerusalem Crosses as depicted in FIG. 3, or some other periodic metallic pattern such as parallel or perpendicular hash marks. The metallic pattern 140 imposes a complex impedance boundary condition to the surface which traps electromagnetic radiation into waves tightly bound to the surface. A thin dielectric substrate 141 sits between the textured metallic layer 140 and a metallic ground plane 142. The surface impedance is determined by the metallic pattern and the thickness of the dielectric and its electrical properties, such as its permittivity, resistivity, and permeability.

Figure 7:
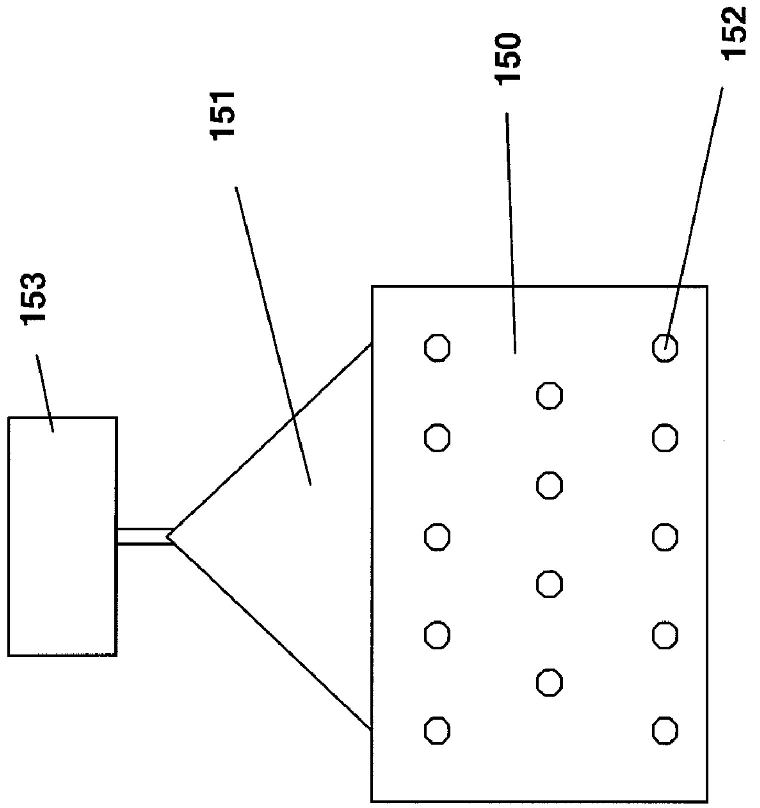
FIG. 7 depicts a high power surface-wave coupler integrated to a surface-wave medium having an array of microwave plasma generators/field enhancement points for producing atmospheric plasma.

FIG. 7 depicts a high power surface-wave coupler 151 integrated to a surface-wave medium 150 having an array of microwave plasma generators/field enhancement points 152 for producing atmospheric plasma. The surface-wave medium 150 can be built into the surface, laminated to the surface, or otherwise attached to the surface. In an exemplary embodiment of the present invention, a metasurface 150 is provided for creating a large-scale plasma around that surface. The metasurface 150 supports surface-wave propagation at microwave frequencies and contains integral microwave resonant structures 152 that locally enhance electric fields, resulting in production of atmospheric plasma. Plasmas are known to absorb microwave radiation and therefore the exemplary embodiment can be used to shield structures or vehicles from radar interrogation.

Such a metasurface 150 does not require complex wiring or power routing schemes to create a large array of field enhancement points 152 across a surface because the surface-wave propagation across the metasurface uniformly distributes the microwave power across the entire surface and the integrated field enhancement points 152 are powered directly by the surface waves.

As depicted in FIG. 7, the metasurface includes two main components: (1) a surface-wave guiding metasurface 150 and (2) an array of field enhancement points 152. The array of field enhancement points 152 can be integral with the surface or distinct components that are separately added to the surface. The surface-wave guiding metasurface 150 can include a dielectric substrate with a repeating (e.g., periodic) or aperiodic metallic pattern. In another exemplary embodiment, the dielectric substrate can have a metallic ground plane on the other side. The surface-wave guiding medium 150 is capable of supporting high-power microwave-frequency surface waves. The most convenient microwave frequency to design for is 2.45 GHz because high-power (~1 kW), inexpensive, and commercially available magnetron sources are available at this frequency.

The array of field enhancement points 152 are disposed periodically on the surface-wave guiding surface 150. The field enhancement points 152 are powered by the microwave-frequency surface waves. Each field enhancement point 152 is capable of producing atmospheric plasma. Together, all of the field enhancement points 152 produce a plasma cloud that substantially covers the entire surface.

The field enhancement point 152 is comprised of a resonant structure that produces a high field region, which ionizes the air in its vicinity. The field enhancement points 152 can be separate from or integrated into the surface wave medium 150. When integrated, the field enhancement points 152 could be formed by creating a resonant protrusion on each unit cell of the repeating metallic pattern on the dielectric. The protrusions would be resonant at the microwave feed frequency (nominally 2.45 GHz), and would create a high-field, high-frequency electrode which would ionize the surrounding gaseous medium. The microwave power source 153 may be provided by any high power microwave generator, nominally a 2.45-GHz magnetron, and is coupled to the surface wave medium 150 with a high-power microwave coupler 151.

Figure 8:
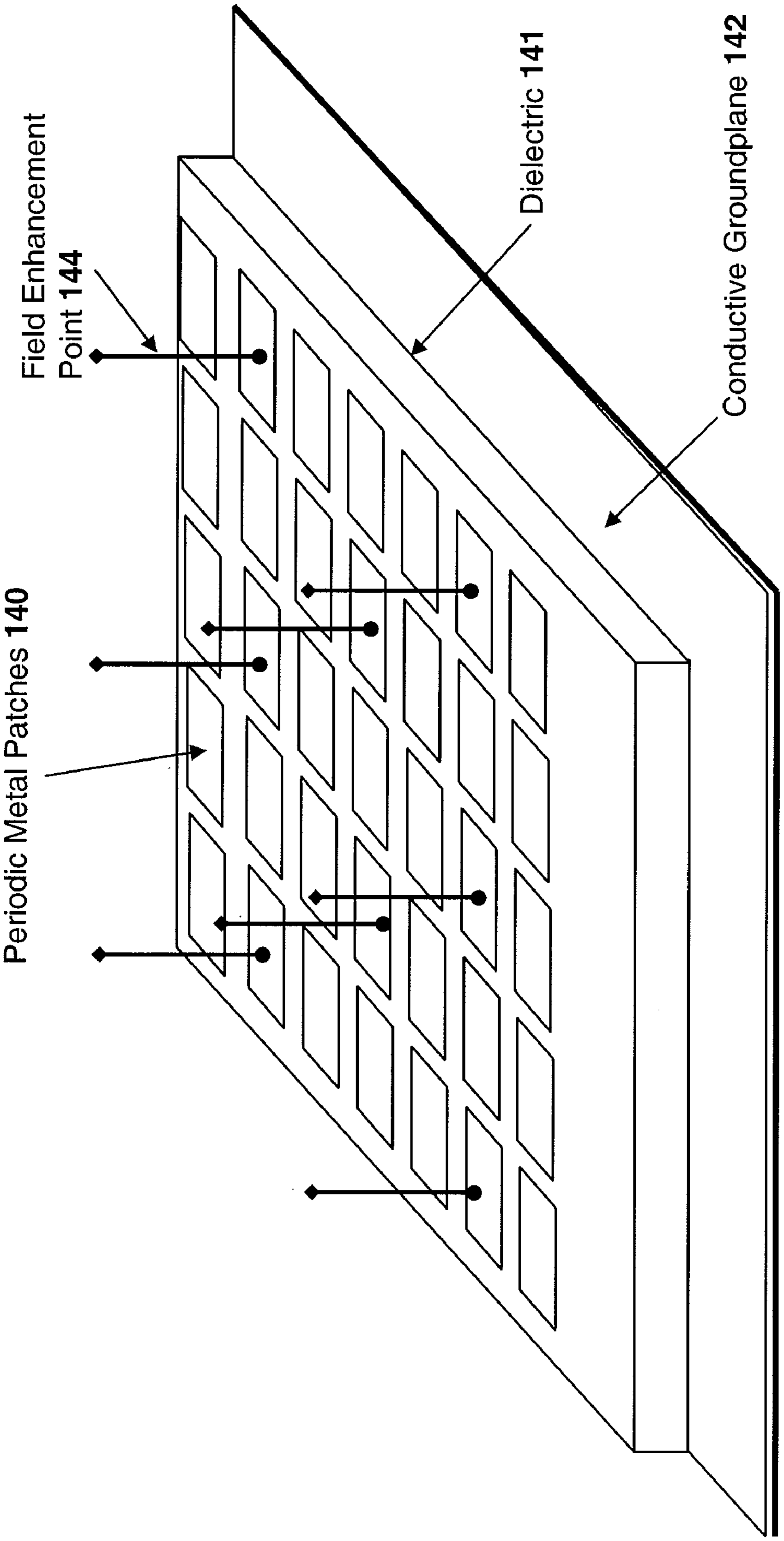
FIG. 8 is another view of a high power surface-wave coupler integrated to a surface-wave medium showing the array of field enhancement points for producing atmospheric plasma.

FIG. 8 is another view of a high power surface-wave coupler integrated to a surface-wave medium showing the array of field enhancement points 144 for producing atmospheric plasma. The surface-wave medium includes a periodic metallic pattern 140 on a dielectric material 141. The periodic metallic pattern 140 may be squares, Jerusalem Crosses, or some other periodic metallic pattern such as parallel or perpendicular hash marks. The metallic pattern 140 imposes a complex impedance boundary condition to the surface which traps electromagnetic radiation into waves tightly bound to the surface. A thin dielectric substrate 141 sits between the textured metallic layer 140 and a metallic ground plane 142. The surface impedance is determined by the metallic pattern and the thickness of the dielectric and its electrical properties, such as its permittivity, resistivity, and permeability. The surface-wave medium further includes a plurality of field enhancement points 144 as discussed in relation to FIG. 7.

The preceding paragraphs describe structures for implementing a surface-wave medium. However, a person skilled in the art will realize a surface-wave medium may be constructed in other ways now known or in others ways yet to be developed. Consequently, a surface-wave medium should be interpreted as any surface capable of supporting surface waves, unless otherwise limited.

While the invention has been described in terms of exemplary embodiments, it is to be understood that the words which have been used are words of description and not of limitation. As is understood by persons of ordinary skill in the art, a variety of modifications can be made without departing from the scope of the invention defined by the following claims, which should be given their fullest, fair scope.

What is claimed is:

1. A method of generating a plasma on a surface, comprising:

laminating a surface-wave medium to a surface for propagating electromagnetic surface waves, the surface-wave medium including a conductive ground plane on the surface, a dielectric on the conductive ground plane, and a metallic pattern on the dielectric for increasing an inductive reactance of the surface-wave medium;

providing a microwave power source, the electromagnetic surface waves being microwave surface waves;

coupling the microwave power source to the surface-wave medium with a coupler; and locating a plurality of field enhancement points on the surface-wave medium, the plurality of field enhancement points being comprised of microwave resonant structures that couple to the electromagnetic surface waves.

2. The method of claim 1, wherein the microwave power source is a 2.45 GHz magnetron.

3. The method of claim 1, further comprising:

powering the plurality of field enhancement points with transmitted electromagnetic surface waves.

4. The method of claim 1, further comprising:

creating a substantially surface-covering plasma layer that transforms fields of the electromagnetic surface waves into high-field regions that ionize surrounding air or a gaseous medium.

5. The method of claim 1, wherein the metallic pattern is a periodic metallic pattern of squares, rectangles, parallel or perpendicular hash marks, or Jerusalem crosses.

6. The method of claim 1, wherein the metallic pattern is aperiodic.

7. A plasma generating apparatus, comprising:

a surface-wave medium laminated to a surface for propagating electromagnetic surface waves, the surface-wave medium including a dielectric and a metallic pattern on the dielectric for increasing an inductive reactance of the surface-wave medium;

a plurality of field enhancement points on the surface-wave medium;

a microwave power source; and a coupler coupling the microwave power source to the surface-wave medium.

8. The plasma generating surface as claimed in claim 7, wherein the metallic pattern is a periodic metallic pattern of squares, rectangles, parallel or perpendicular hash marks, or Jerusalem crosses.

9. The plasma generating surface as claimed in claim 7, wherein the metallic pattern is aperiodic.

10. The plasma generating surface as claimed in claim 7, wherein the surface-wave medium includes a conductive ground plane between the surface and the dielectric.

11. The plasma generating surface as claimed in claim 7, wherein the plurality of field enhancement points are powered by the electromagnetic surface waves and wherein the electromagnetic surface waves are microwave surface waves.

12. The plasma generating surface as claimed in claim 7, wherein the plurality of field enhancement points are adapted to create a substantially surface-covering plasma layer.

13. The plasma generating surface as claimed in claim 7, wherein the plurality of field enhancement points are comprised of microwave resonant structures that couple to the electromagnetic surface waves.

14. The plasma generating surface as claimed in claim 7, wherein the plurality of field enhancement points are adapted to transform fields of the electromagnetic surface waves into high-field regions that ionize surrounding air or a gaseous medium.

15. The plasma generating surface as claimed in claim 7, wherein the microwave source is a 2.45 GHz magnetron.

16. A plasma generating apparatus, comprising:

a surface-wave medium laminated to a surface for propagating electromagnetic surface waves, the surface-wave medium including a conductive ground plane on the surface, a dielectric on the conductive ground plane, and a metallic pattern on the dielectric for increasing an inductive reactance of the surface-wave medium;

a plurality of field enhancement points on the surface-wave medium for creating a substantially surface-covering plasma layer that transforms fields of the electromagnetic surface waves into high-field regions that ionize surrounding air or a gaseous medium, the plurality of field enhancement points powered by the electromagnetic surface waves, the plurality of field enhancement points being comprised of microwave resonant structures that couple to the electromagnetic surface waves, the electromagnetic surface waves being microwave surface waves;

a microwave power source; and a coupler coupling the microwave power source to the surface-wave medium.

17. The plasma generating surface as claimed in claim 16, wherein the microwave power source is a 2.45 GHz magnetron.

18. The plasma generating surface as claimed in claim 16, wherein the metallic pattern is a periodic metallic pattern of squares, rectangles, parallel or perpendicular hash marks, or Jerusalem crosses.

19. The plasma generating surface as claimed in claim 16, wherein the metallic pattern is aperiodic.

* * * * *